US010933171B2

(12) United States Patent
Uraoka et al.

(10) Patent No.: US 10,933,171 B2
(45) Date of Patent: Mar. 2, 2021

(54) COLLAGEN SOL FOR SUBMUCOSAL LOCAL INJECTION

(71) Applicants: Tokyo Metropolitan Industrial Technology Research Institute, Tokyo (JP); National University Corporation Gunma University, Gunma (JP)

(72) Inventors: Toshio Uraoka, Tokyo (JP); Naohisa Yahagi, Tokyo (JP); Shunji Yunoki, Tokyo (JP); Yoshimi Ohyabu, Tokyo (JP); Takefumi Narita, Tokyo (JP)

(73) Assignees: Tokyo Metropolitan Industrial Technology Research Institute, Tokyo (JP); National University Corporation Gunma University, Gunma (JP)

(*) Notice: Subject to any disclaimer, the term of this patent is extended or adjusted under 35 U.S.C. 154(b) by 0 days.

(21) Appl. No.: 16/461,552

(22) PCT Filed: Nov. 16, 2017

(86) PCT No.: PCT/JP2017/041244
§ 371 (c)(1),
(2) Date: May 16, 2019

(87) PCT Pub. No.: WO2018/092837
PCT Pub. Date: May 24, 2018

(65) Prior Publication Data
US 2019/0290808 A1 Sep. 26, 2019

(30) Foreign Application Priority Data
Nov. 17, 2016 (JP) .............................. JP2016-224258

(51) Int. Cl.
*A61L 31/04* (2006.01)
*A61K 31/352* (2006.01)
*A61L 31/16* (2006.01)
*A61K 47/22* (2006.01)
*A61K 9/06* (2006.01)
*A61B 17/32* (2006.01)
*A61L 31/14* (2006.01)
*A61L 33/12* (2006.01)
*A61B 17/28* (2006.01)
*A61K 47/42* (2017.01)
*A61K 47/02* (2006.01)

(52) U.S. Cl.
CPC ............ *A61L 31/047* (2013.01); *A61B 17/28* (2013.01); *A61B 17/32* (2013.01); *A61K 9/06* (2013.01); *A61K 31/352* (2013.01); *A61K 47/02* (2013.01); *A61K 47/22* (2013.01); *A61K 47/42* (2013.01); *A61L 31/04* (2013.01); *A61L 31/044* (2013.01); *A61L 31/14* (2013.01); *A61L 31/16* (2013.01); *A61L 33/12* (2013.01); *A61B 17/320016* (2013.01)

(58) Field of Classification Search
CPC .......... A61B 17/320016; A61K 31/352; A61L 31/044; A61L 31/047; A61L 31/16; F15B 13/0402; F15B 13/042; F15B 13/0436; F15B 13/0438; F15B 13/044; F15B 9/06; F16K 11/0708; F16K 31/04; F16K 31/124; F16K 31/426; Y10T 137/0486; Y10T 137/86598
See application file for complete search history.

(56) References Cited

U.S. PATENT DOCUMENTS

| 8,066,689 | B2* | 11/2011 | Mitelberg ......... A61B 1/00165 604/509 |
| 8,491,472 | B2* | 7/2013 | Mitelberg ......... A61B 1/00165 600/115 |
| 2002/0091445 | A1 | 7/2002 | Sung |
| 2006/0246033 | A1* | 11/2006 | Ninan ................. A61K 9/0019 424/85.5 |
| 2007/0078108 | A1 | 4/2007 | Hayashi et al. |
| 2009/0018603 | A1* | 1/2009 | Mitelberg ......... A61B 17/3468 607/40 |
| 2009/0018604 | A1* | 1/2009 | Mitelberg ......... A61B 1/00165 607/40 |
| 2015/0105336 | A1 | 4/2015 | Takamura et al. |

FOREIGN PATENT DOCUMENTS

| EP | 1352661 A1 | 10/2003 |
| EP | 2783709 A1 | 10/2014 |
| JP | 2014103985 A | 6/2014 |
| JP | 2016077410 A | 5/2016 |
| WO | 2005037292 A | 4/2005 |

(Continued)

OTHER PUBLICATIONS

Narita et al. In situ gelation properties of a collagen—genipin sol with a potential for the treatment of gastrointestinal ulcers. Medical Devices: Evidence and Research 2016:9 429-439, (Year: 2016).*
Yanoki et al. Temperature-Responsive Gelation of Type I Collagen Solutions Involving Fibril Formation and Genipin Crosslinking as a Potential Injectable Hydrogel. International Journal of Biomaterials. vol. 2013, 14 pages. (Year: 2013).*
Ono et al. Endoscopic submucosal dissection for superficial esophageal neoplasms. World J Gastrointest Endosc May 16, 2012; vol. 4, No. 5, pp. 162-166 (Year: 2012).*

(Continued)

*Primary Examiner* — Marcela M Cordero Garcia
(74) *Attorney, Agent, or Firm* — Suzannah K. Sundby, Esq.; Canady + Lortz LLP

(57) ABSTRACT

Object of the present invention is to provide a safe sol for submucosal local injection which gels and creates a mucosal elevation having a high retention rate of mucosal elevation height when locally injected into a digestive submucosa. Provided is a sol for submucosal local injection containing from 0.2 mass % to 1.2 mass % of a collagen, water, a buffer, and from 200 mM to 420 mM sodium chloride.

12 Claims, 4 Drawing Sheets

(56) References Cited

FOREIGN PATENT DOCUMENTS

| WO | 2013077357 A | 5/2013 |
|---|---|---|
| WO | 2013133413 A | 9/2013 |

OTHER PUBLICATIONS

Soetikno et al. Endoscopic mucosal resection. Gastrointestinal Endoscopy. vol. 57, No. 4, pp. 567-579. (Year: 2003).*
International Search Report received in PCT/JP2017/041244 dated Jan. 23, 2018.
Written Opinion received in PCT/JP2017/041244 dated Jan. 23, 2018.
Alkan et al., "Histological response to injected gluteraldehyde cross-linked bovine collagen based implant in a rat model", Feb. 18, 2006, pp. 1-5, vol. 6, No. 3, Publisher: BMC Urol.
Al-Taie et al., "Efficacy of submucosal injection of different solutions inclusive blood components on mucosa elevation for endoscopic resection", Apr. 17, 2012, pp. 43-48, vol. 5, Publisher: Clin Exp Gastroenterol.
Eun et al., "Effectiveness of Sodium Alginate as a Submucosal Injection Material for Endoscopic Mucosal Resection in Animal", Jun. 30, 2007, pp. 27-32, vol. 1, No. 1, Publisher: Gut Liver.
Jung et al., "Submucosal injection solutions for endoscopic mucosal resection and endoscopic submucosal dissection of gastrointestinal neoplasms", Sep. 13, 2013, pp. 73-77, vol. 2, No. 2, Publisher: Gastrointestinal Intervention.
Yunoki et al., "A novel fabrication method to create a thick collagen bundle composed of uniaxially aligned fibrils: An essential technology for the development of . . . ", Feb. 26, 2015, pp. 3054-3065, vol. 103A, Publisher: J Biomed Mater Res Part A.

* cited by examiner retention rate of mucosal elevation height (%) = $h_t / h_0 \times 100$

COLLAGEN SOL FOR SUBMUCOSAL LOCAL INJECTION

TECHNICAL FIELD

The present invention relates to a sol for in vivo injection useful as a local injection for forming submucosal elevation, more specifically, a collagen sol for submucosal local injection which is injected into the submucosa to create a mucosal elevation upon resection of a lesion such as tumor and thereby carry out the resection easily and safely.

BACKGROUND ART

Cancers, such as gastric cancer and colon cancer, which emerge in the digestive tract are known to appear in the mucosal layer which is the innermost layer of the digestive tract and gradually infiltrate into the submucosal layer below the mucosal layer and then, the muscular layer below the submucosal layer. For removing the early-stage cancer, endoscope treatment technology called "endoscopic mucosal resection (EMR)" or "endoscopic submucosal dissection (ESD)" is used.

In EMR, a liquid such as saline is locally injected (local injection) into the submucosa of a lesion to elevate the lesion to be resected. Then, a metal wire called "snare" is placed around the elevated site, the mucosa is resected by strangulation and energization, and hemostatic procedure at the ulcer site is performed. Whether or not the lesion such as cancer is collectively resected is determined by the histopathological diagnosis of the site thus resected (FIG. 1).

In ESD, after a resection part around a lesion is marked, submucosal local injection of a liquid is performed to elevate the lesion to be resected as in EMR. Then, with a knife exclusively used for ESD, the mucosal layer including the lesion is dissected collectively with the submucosal layer and hemostatic procedure for the ulcer site is performed. Whether or not the lesion such as cancer is collectively resected is determined by the histopathological diagnosis of the site thus dissected (FIG. 2).

Saline frequently used as a local injection for creating a submucosal elevation in EMR, ESD, or the like has such a problem as quick attenuation of elevation height. Attenuation of the elevation height during dissection of the submucosal layer by ESD makes it difficult to apply a knife to a desirable depth of the submucosal layer and therefore it becomes a cause for insufficient removal of the lesion or perforation. To overcome this problem, a local injection for enhancing the viscosity of an injection liquid and thereby suppressing diffusion thereof has been studied. More specifically, a local injection thickened with hyaluronic acid, glycerol, dextrose, hydroxypropyl cellulose, chitosan, or the like has been studied and some of them have already been commercialized and clinically used (Non-Patent Document 1). These products however have a low retention rate of mucosal elevation height so that a local injection which gels in the submucosa after being injected locally has also been studied.

For example, there is a report that local injection of whole blood (blood collected from a patient) causes less attenuation of elevation height (Non-Patent Document 2). In addition, there are reports on an example using an aqueous solution of sodium alginate as a submucosal local injection (Non-Patent Document 3), an attempt of exposing chitosan having a photo-reactive group introduced therein to ultraviolet light after local injection to cause gelation of it in the submucosa (Patent Document 1), a technology of making use of pseudoplasticity of a polysaccharide such as xanthan gum and delivering, via a catheter, a highly viscous liquid which hardly diffuses in the submucosa (Patent Document 2), and the like.

The present inventors have, on the other hand, already found that a specific aqueous collagen/genipin mixed solution has gelation properties in which the collagen forms fibrils at a temperature near the body temperature and then genipin crosslinking is introduced (Patent Document 3). The present inventors have also found that adjustment of the concentration of an inorganic salt can increase the gelation rate of a specific aqueous collagen solution (Patent Document 4 and Non-Patent Document 4). Effectiveness of these aqueous solutions to a particular medical use has however not yet been known.

CITATION LIST

Patent Documents

Patent Document 1: WO2005/037292
Patent Document 2: WO2013/077357
Patent Document 3: JP 2014-103985 A
Patent Document 4: JP 2016-077410 A

Non-Patent Document

Non-Patent Document 1: Yoon suk Jung et al., Gastrointestinal Intervention, 2013 2(2), 73-77
Non-Patent Document 2: Al-Taie et al, Clinical and Experimental Gastroenterology, 2012:5, 43-48
Non-Patent Document 3: Eun et al., Gut and Liver 2007: 1(1) 27-32
Non-Patent Document 4: Yunoki et al. Journal of Biomedical Materials Research Part A Volume 103, Issue 9, pages 3054-3065, 2015

SUMMARY

Problem to be Solved

The conventional method of locally injecting the whole blood described in Non-Patent Document 2 has problems such as possibility of contamination of the collected blood and a limited collection amount. The aqueous solution of sodium alginate described in Non-Patent Document 3 does not have a sufficient retention rate of mucosal elevation height because it has a half time of elevation height about 10 minutes after local injection. The method described in Patent Document 1 has possibility of histological damages and is therefore has a problem in safety because the mucosal surface is exposed to strong ultraviolet light. In addition, a medical institution should be equipped with an ultraviolet irradiation apparatus. The highly viscous liquid described in Patent Document 2 does not gel in the submucosa so that elevation attenuates time-dependently.

As described above, there is no safe local injection capable of gelling when locally injected into the submucosa of the digestive tract and creating a mucosal elevation having a high retention rate of mucosal elevation height.

In such a background, an object of the present invention is to provide a safe sol for submucosal local injection that can be used in EMR, ESD, or the like and gels when locally injected into the submucosa of the digestive tract to create a mucosal elevation having a high retention rate of mucosal elevation height.

With a view to achieving the above-described object, the present inventors have found that a sol containing a specific concentration of a collagen, water, a buffer, and a specific concentration of sodium chloride gels promptly and creates a mucosal elevation when locally injected into the submucosa and a retention rate of the mucosal elevation 60 minutes after gastric submucosal local injection becomes more than 70% of that just after the injection and the attenuation of the elevation stops in 60 minutes after the gastric submucosal local injection. Further, the present inventors have found that the gel is integrated with the submucosal layer so that it is suited for the removal of a lesion that has infiltrated even to the submucosal layer.

The present invention relates to the followings.

[1] A sol for submucosal local injection, containing from 0.2 mass % to 1.2 mass % of a collagen, water, a buffer, and from 200 mM to 420 mM sodium chloride.

[2] The sol for submucosal local injection described in [1], further containing from 40 mg/L to 1400 mg/L of genipin or a genipin derivative.

[3] The sol described in [1], having a pH from 6.0 to 9.0 and containing a phosphate as the buffer.

[4] The sol described in any of [1] to [3] containing from 40 mg/L to 1400 mg/L of genipin or a genipin derivative and from 220 mM to 310 mM sodium chloride, wherein the sol gels to create a mucosal elevation when locally injected into submucosa.

[5] An endoscope system for endoscopic mucosal resection or endoscopic submucosal dissection, having a unit for locally injecting the sol described in any of [1] to [4].

The present invention also relates to the followings:

[6] A kit for forming the sol described in any of [1] to [4], containing a collagen, sodium chloride, and a buffer.

[7] A method of resecting a lesion, including a step of submucosally injecting the sol described in any of [1] to [4] and a step of resecting the lesion.

[8] A method described in [7] wherein the step of resecting the lesion includes a step of dissecting the submucosal layer by EMR or ESD.

Advantageous Effects of Invention

The present invention makes it possible to provide a safe local injection that promptly gels and creates a mucosal elevation having a high retention rate of mucosal elevation height when submucosally and locally injected. The sol of the present invention can be injected/formed into a gel without the necessity of an operation which may cause histological damages or a special apparatus; and different from blood preparations, it is free from the possibility of contamination or limitation on an amount to be secured.

BRIEF DESCRIPTION OF DRAWINGS

FIG. 5A shows a measured value of elevation height. FIG. 5B shows a retention rate relative to initial elevation height.

FIG. 6A shows a measured value of elevation height. FIG. 6B shows a retention rate relative to initial elevation height.

DESCRIPTION OF EMBODIMENTS

Figure 1:
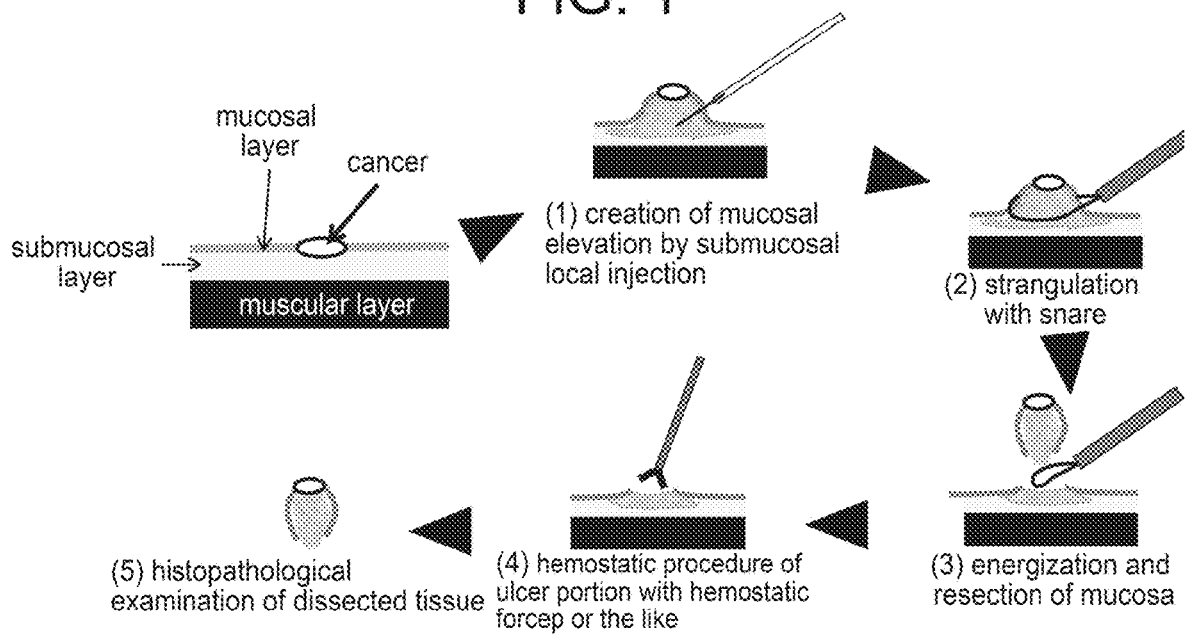
FIG. 1 shows a schematic view of EMR.
Figure 2:
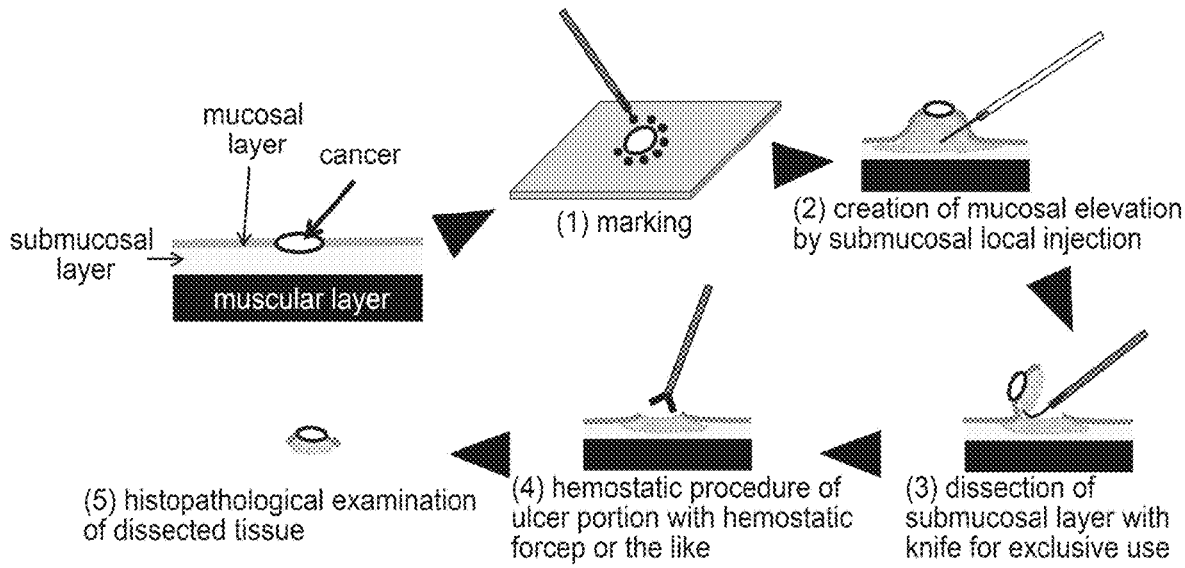
FIG. 2 shows a schematic view of ESD.

An embodiment for carrying out the invention (which may hereinafter be called "present embodiment", simply) will hereinafter be described in detail. The present embodiment described below is an example for describing the present invention and does not intend to limit the present invention only to this present embodiment.

The sol of the present embodiment is a sol for submucosal local injection that gels and creates a mucosal elevation when locally injected into the submucosa. It is a sol for submucosal local injection (a pharmaceutical composition for submucosal local injection, a sol composition for submucosal local injection) that contains from 0.2 mass % to 1.2 mass % of a collagen, water, a buffer, and from 200 mM to 420 mM sodium chloride and may further contain from 40 mg/L to 1400 mg/L of genipin or a genipin derivative.

Although the collagen contained in the sol of the present embodiment is not particularly limited, it is preferably a telopeptide-removed collagen hard to proceed with fibril formation near the room temperature and it is more preferably composed substantially of the telopeptide-removed collagen. The telopeptide-removed collagen is obtained by enzymatically degrading and removing a telopeptide present at both ends of the collagen molecule by a proteolytic enzyme. For example, it is obtained by degrading and removing a telopeptide present at both ends of the collagen molecule by pepsin digestion. Of telopeptide-removed collagens, telopeptide-removed collagens derived from mammals approved as a raw material for a medical apparatus are preferred, with telopeptide-removed collagens already used clinically and obtained from the porcine dermis excellent in thermal stability being more preferred. Telopeptide-removed collagens are commercially available as an alternate name, that is, atelocollagen and they are easily available.

Collagens are not particularly limited insofar as they are collagens having fibril forming ability (fibril-forming collagens). Of the fibril-forming collagens, a Type I collagen constituting the bone, skin, tendon and ligament, a Type II collagen constituting the cartilage, and a Type III collagen contained in the tissue composed of the Type I collagen are preferably used from the viewpoint of their availability, plentiful research results or similarly to the tissue to which the prepared gel is applied. The collagen may be obtained by extraction/purification from the tissue by the conventional method or it may be a commercially available one. The collagen may be a purified product of any of the above-described types or a mixture of a plurality of the above-described types.

The denaturation temperature of the collagen is preferably 32° C. or more, more preferably 35° C. or more, further more preferably 37° C. or more. At the denaturation temperature of 32° C. or more, the fluidity of the sol at room temperature can be kept for a longer period of time and at the same time, in vivo denaturation of the collagen is suppressed. The upper limit of the denaturation temperature of the collagen is not particularly limited, but it is preferably 50° C. or less, more preferably 45° C. or less, still more preferably 41° C. or less. The denaturation temperatures not more than the above-described upper limit can allow the gelation at the time of submucosal local injection to proceed more promptly. The denaturation temperature of the collagen is measured by the conventional method based on a change in circular dichroism, optical rotation, or a viscosity with an increase in the temperature of an aqueous collagen solution. The denaturation temperature of the collagen may be adjusted by selecting a collagen having a denaturation temperature within the above-described value range.

The sol of the present embodiment contains an aqueous collagen solution containing the collagen and water and from the viewpoint of the sol retentivity for locally causing gelation at a locally injected site, a sol having a high collagen concentration is desired. When the sol has a too low collagen concentration, the resulting sol has a reduced viscosity and dissipation of the sol from the introduced site may occur before gelation. In addition, a gel obtained by gelation of a sol having a higher collagen concentration has improved hardness so that from the viewpoint of retaining the elevation height, the sol having a high collagen concentration is desired.

On the other hand, from the viewpoint that the gel obtained by gelation is integrated with the submucosal layer, a sol having a low collagen concentration is desired. A sol having a too high viscosity sometimes becomes inferior in invasiveness into the submucosal layer and is preferentially sent to an interlayer (for example, a layer between a mucosal layer and a submucosal layer or between a submucosal layer and a muscular layer) to become a gel without integration. When the gel is not integrated with the submucosal layer, it may become difficult to remove the lesion which has infiltrated into the submucosal layer. Also from the viewpoint of performing local injection conventionally through a thin tube (catheter, injection needle, or the like), a sol having a low collagen concentration is desired. With an increase in the collagen concentration, the sol has a higher viscosity and has increased extrusion resistance, making it difficult to deliver it, though depending on the diameter or length of the thin tube.

From the above-described viewpoints, the concentration of the collagen in the sol of the present embodiment is from 0.2 mass % to 1.2 mass %, preferably from 0.3 mass % to 1.1 mass %, more preferably from 0.4 mass % to 1.0 mass %, each based on the total amount of the sol.

Since the sol of the present embodiment contains a predetermined concentration of sodium chloride which is an inorganic salt, fibril formation of the collagen is accelerated at the time when the sol is brought into contact with the tissue and the sol gels promptly in response to the body temperature and retains the elevation height.

The concentration of sodium chloride contained in the sol can be adjusted as needed to fall within a range of from 200 mM to 420 mM that is higher than a physiological salt concentration (140 mM). The concentration is adjusted to preferably from 220 mM to 310 mM and, for example, around 230 mM. When the concentration of sodium chloride is less than the physiological salt concentration, it takes long time for gelation of a locally injected collagen sol and diffusion of the sol may easily lead to attenuation of elevation height. When the concentration of sodium chloride exceeds 420 mM, on the other hand, the collagen acquires fibril formation ability near the room temperature and the sol may easily lose its fluidity in the thin tube. By adjusting the concentration of sodium chloride to fall within the above-described range, the locally injected sol gels promptly in response to the body temperature and diffusion of the gel can be prevented.

The sol of the present embodiment has a pH (pH at 23° C., which equally applies to that described herein unless otherwise particularly specified) of from 6.0 to 9.0, more preferably from 6.5 to 8.0. The fibril formation of a collagen is known to vigorously occur near neutral. By adjusting the pH to fall within the predetermined range, fibril formation of a collagen can be accelerated more. The pH can be adjusted by the conventional method, for example, by adjusting the concentration of an inorganic salt contained in the sol, preferably the concentration of sodium chloride and sodium hydrogen phosphate or by adding a strong acid and/or a strong alkali such as hydrochloric acid or sodium hydroxide. The pH can be measured by a known pH meter (for example, "NAVIh F-71", trade name; product of HORIBA).

The sol of the present embodiment contains a buffer for maintaining its pH or the like. Although the buffer is not particularly limited insofar as the sol has desired properties, examples include phosphates, acetates, borates, HEPES and Tris. As the phosphates, sodium phosphate, sodium hydrogen phosphate (collective term for sodium dihydrogen phosphate and disodium hydrogen phosphate), potassium hydrogen phosphate (collective term for potassium dihydrogen phosphate and dipotassium hydrogen phosphate) and the like can be used. As the acetates, sodium acetate and the like can be used, while as the borates, sodium borate and the like can be used. They can each be used in combination with sodium hydroxide or the like serving for pH adjustment. Alternatively, a buffer solution such as a sodium chloride-containing phosphate buffer solution (NPB) using the above-described sodium chloride and buffer in combination may be used.

Of these buffers, phosphates and NPB having a phosphate therein are particularly preferred. The phosphates have such advantages that they are excellent in buffering ability at pH from 6 to 9 at which fibril formation of a collagen occurs vigorously and their safety to living bodies has been confirmed as can be understood from that they are contained in a cell washing solution such as phosphate buffered saline.

The concentration of the buffer is not particularly limited insofar as the pH is kept within a desired range and the sol has desired properties.

From the viewpoint of allowing the buffer to exhibit a pH buffering effect sufficiently, the concentration of the buffer can be adjusted to 5 mM or more. When the concentration of the buffer becomes too high, the salt in the buffer solution may precipitate before preparation of a sol or excessive increase in the ionic strength may bring about histological damages upon use of the sol. The concentration of the buffer can therefore be adjusted to 140 mM or less. The concentration of the buffer is preferably more than 10 mM to less than 120 mM, for example, from 20 mM to 110 mM. The concentration is more preferably from 30 mM to 100 mM. Adjustment of the concentration of the buffer to fall within the above-described range facilitates retention of the pH of the sol within a range of from 6.0 to 9.0, making it possible to allow the sol to exhibit the effect of the sol of the present embodiment, that is, retention of the fluidity of the sol at the time of local injection and prompt gelation in response to the body temperature after local injection to create a mucosal elevation and at the same time, making it possible to suppress precipitation of a salt or histological damages.

When the sol comes into contact with the tissue, it gels, responding to the body temperature. In order to enhance the mechanical strength of the gel and enhance the stability of a mucosal elevation during the step of dissecting the submucosal layer in EMR, ESD, or the like, the above-described sol may contain genipin or a genipin derivative as a crosslinking agent of the collagen. In ESD, a conventional solution to be used for creating a mucosal elevation may escape during the dissection of the submucosal layer with a knife, and thereby accelerating attenuation of elevation height. Time necessary for ESD including creation of a mucosal elevation or difficulty of ESD tends to vary depending on the site of the digestive tract. It is known that, for example, compared with the stomach having a thick muscular layer, the large intestine having a thin wall thickness tends to have a high incidence of perforation by ESD. Addition of genipin or a genipin derivative as a crosslinking agent not only increases the retention rate of mucosal elevation height of the submucosal elevation but also enhances the mechanical strength of the gel to keep a stable elevation even during the dissection of the submucosal layer with a knife. Genipin which is derived from a plant and is thought to have low cellularity is aglycone derived from geniposide. It can be obtained, for example, by oxidation, reduction and hydrolysis of geniposide or by enzymatic hydrolysis of geniposide. Geniposide is an iridoid glycoside contained in gardenia of the family Rubiaceae and is extracted from the gardenia. Genipin is represented by the molecular formula of $C_{11}H_{14}O_5$. It may be obtained by synthesis by the conventional method or a commercially available product may be used. Genipin may be derivatized insofar as derivatization does not inhibit the desired properties of the sol of the present embodiment and its crosslinking effect is ensured. As the derivatives of genipin, for example, those described in JP 2006-500975 T can be used. The term "genipin" as used herein also means a polymer of genipin. It is known that genipin is polymerized under various conditions. Although no particular limitation is imposed on the polymerization conditions and method thereof, for example, a method of polymerizing it by aldol condensation under strong alkali conditions (Mi et al. Characterization of ring-opening polymerization of genipin and pH-dependent crosslinking reactions between chitosan and genipin. Journal of Polymer Science: Part A: Polymer Chemistry, Vol. 43, 1985-2000 (2005)) can be used.

When the sol of the present embodiment contains genipin or a derivative thereof, its concentration can be set at 1400 mg/L or less, preferably from 40 mg/L to 1400 mg/L, for example, from 100 mg/L to 1000 mg/L from the viewpoint of keeping the fluidity of the sol at the time of local injection. Adjustment of the genipin concentration within the above-described range makes it possible not only to enhance the retention rate of mucosal elevation height of the submucosal elevation while keeping fluidity of the sol at the time of local injection but also to enhance the mechanical strength of the gel to maintain stable elevation even during the dissection of the submucosal layer with a knife.

The sol of the present embodiment may further contain various solvents and additives used for a conventional aqueous collagen solution. Examples of such solvents and additives include acids such as diluted hydrochloric acid, citric acid, and acetic acid.

These additives or solvents may be used either alone or in combination of two or more. The respective contents of the additive and the solvent in the sol are not particularly limited insofar as they fall within a range not impairing the desired properties of the sol of the present embodiment.

The sol of the present embodiment gels and creates a mucosal elevation when locally injected into the submucosa so that it is useful in endoscopic treatment using an energy device such as ESD or EMR. One aspect of the present embodiment therefore relates to an endoscopic system for ESD or EMR equipped with a means of locally injecting the sol of the present embodiment.

For example, in ESD which is one of endoscopic treatments, incidence of perforation as an accidental symptom has become a problem. The sol of the present embodiment promptly gels in the submucosa after local injection thereto to create a mucosal elevation having a high retention rate of mucosal elevation height so that a risk of incidence of perforation can be reduced. This facilitates collective resection of a lesion.

The retention rate of mucosal elevation height can be calculated based on the following equation including an initial height ($h_0$) of elevation height just after local injection and elevation height ($h_t$) after a predetermined time (t), as shown later in Examples and FIG. 3.

Retention rate (%) of elevation height=$h_t/h_0$×100

The necessary retention rate of mucosal elevation height varies depending on the degree of bleeding or the number of lesions. In general, when bleeding is not so severe, ESD for a single lesion is often finished within 60 minutes from the local injection of a submucosal local injection until hemostatic treatment and the retention rate of mucosal elevation height 60 minutes after the local injection may be one evaluation standard of a submucosal local injection. In one aspect, the sol of the present embodiment has preferably a retention rate of mucosal elevation height of 70% or more, more preferably 80% or more, particularly preferably 90% or more, each 60 minutes after the local injection.

With respect to the retention rate of mucosal elevation height, termination of a decrease in elevation height is also desired. In one aspect, the sol of the present embodiment preferably does not cause a statistically significant decrease in elevation height between 45 minutes and 60 minutes after the local injection.

The sol of the present embodiment locally injected gels promptly to create a mucosal elevation having a high retention rate of mucosal elevation height so that this facilitates resection of a lesion part larger than a conventional one. When the lesion part is, for example, a cancer, the lesion part remaining without being resected, if any, has the possibility of metastasis. The sol of the present embodiment however can reduce the possibility of such metastasis. The sol of the present embodiment when locally injected into the submucosa can exhibit a hemostatic effect in the submucosal layer because the collagen gels as a result of integration with the submucosal layer. Blood vessels are present in the submucosal layer so that invasion into the submucosal layer by the endoscopic treatment causes bleeding as an accidental symptom. Collagen fibrils have a platelet adhesion effect and collagen fibril powder is clinically used as a hemostatic agent (Avitene, trade name). The sol of the present embodiment exhibits not only a physical hemostatic effect by being integrated with the submucosal layer to form a gel of collagen fibrils and covering the defective blood vessel but also a biochemical hemostatic effect induced by platelet adhesion.

Whether or not the gel is integrated with the submucosal layer can be determined using a method known to those skilled in the art. For example, as shown later in Examples and FIG. 4, it can be determined by whether or not the gel can be observed independently from the submucosal layer on the histological image obtained by tissue fixation 60 minutes after the local injection.

The local injection of the sol of the present embodiment can be performed into the digestive submucosa through an injection needle or the like for endoscopic treatment having a needle at a tip portion of its long thin tube made of plastic or the like and this injection needle is a type of catheter. The sol of the present embodiment has a long fluidity retention time (for example, 10 minutes at room temperature) which permits delivery to the tissue through a long thin tube such as catheter and can be delivered, for example, under an endoscope or a perspective image, for example, through a catheter having an inner diameter of 2.2 mm and a total length of 2.8 m. Although the inner diameter and length of a thin tube to be used for delivery can be changed as needed, depending on the delivery site, viscosity of the sol, or the like, the thin tube may have, for example, an inner diameter of from 0.5 mm to 2.8 mm and a length of from 1 m to 3 m. The sol of the present embodiment has such a property that it can be delivered to the tissue even if a thin tube having a small inner diameter (for example, an inner diameter of from 0.5 mm to 2.5 mm) or a thin tube having a long length (for example, a length of from 1.5 m to 3 m) is used.

For locally forming a gel as described above, conversion of the collagen which has entered the submucosal layer into fibrils (a kind of self-organization) occurs to form a gel (primary gelation). When the sol contains a crosslinking agent such as genipin, a crosslink into the collagen fibril gel is introduced (secondary gelation), and the gel has enhanced strength and chemically bonds between the collagen and the tissue.

The sol of the present embodiment having the above-described properties can be formed, below a lesion, into a gel having a high retention rate of mucosal elevation height and capable of keeping a stable elevation even if invaded by an energy device such as ESD knife. The gel thus formed physically covers the surroundings of the damaged blood vessel therewith and at the same time, exhibits a hemostatic effect, showing platelet adhesion which is a property inherent in collagen fibrils. Further, since the collagen is excellent in safety, biocompatibility, and bioabsorbability, the gel remaining in the submucosal layer after resection of a lesion does not hinder the healing of an ulcer because it is gradually subjected to an action such as hydrolysis or enzymatic degradation, as with a case of a normal collagen.

The sol of the present embodiment may further contain a medicament, depending on the state of an affected part to be locally injected. Although such a medicament is not particularly limited insofar as it can be incorporated in a conventional injectable gel, examples include hemostatic agents such as thrombin and sucralfate, healing promoters such as proton pump inhibitor, cell growth factors such as epithelial cell growth factor, other antibiotics, anti-tumors, and hormone preparations. These medicaments may be used either alone or in combination of two or more. The content of the medicament is not particularly limited insofar as it is within the range that permits exhibition of efficacy of the medicament and does not hinder the desired properties of the gel of the present embodiment.

The present embodiment also relates to a kit for forming the sol. The kit may include a collagen for the formation of a sol, sodium chloride, and a buffer and it may further include genipin if desired. The components constituting the kit may be in dry form so as to be mixed just before use.

The present embodiment also relates to a method of resecting a lesion including a step of locally injecting the sol into the submucosa and a step of resecting the lesion. The step of resecting the lesion may include a step of dissecting the submucosal layer by EMR or ESD. The present embodiment further relates to a method of treating a lesion including these methods. These methods can be carried out, referring to the above description about the sol of the present embodiment.

EXAMPLES

The present embodiment will hereinafter be described more specifically based on Examples and Comparative Examples, but the present invention is not limited to or by the following Examples and Comparative Examples.

[Preparation of Collagen Solution]

A solution of collagen obtained from porcine dermis having a concentration of 1.0 mass % (telopeptide-removed collagen, product of NH Foods, denaturation temperature of collagen: 40° C.) was prepared as a collagen stock solution. The collagen solution was concentrated using an evaporator (water-bath temperature: 29° C.) to obtain a collagen solution having a concentration of 2.4 mass %. The resulting solution was diluted to from 0.5% to 1.5% with diluted hydrochloric acid having a pH 3 and the diluted solution was dispensed in 15-mL centrifuge tubes and stored in a refrigerator.

[Preparation of Aqueous Genipin Solution]

An aqueous genipin solution having a concentration of 24 mM (5430 mg/L) was prepared by dissolving genipin (product of Wako Pure Chemical) in pure water. The resulting aqueous solution was diluted with pure water to prepare aqueous genipin solutions different in concentration.

[Preparation of NPB]

An aqueous solution of disodium hydrogen phosphate having a concentration of 50 mM (containing 140 mM sodium chloride) and an aqueous solution of sodium dihydrogen phosphate having a concentration of 50 mM (containing 140 mM sodium chloride) were prepared using pure water as a solvent. The resulting solutions were stirred and mixed while measuring their pH by a pH meter ("NAVIh F-71", trade name; product of HORIBA) and a 50 mM phosphate buffer solution containing 140 mM sodium chloride and having a pH 7.0 was prepared. The buffer solution thus obtained was defined as 1×NPB. In all the Examples, the pH was measured using the above-described pH meter at 23° C. unless otherwise particularly specified. By a similar operation, 10×NPB (it means NPB having an inorganic salt concentration 10 times that of 1×NPB and this naming method will hereinafter apply to NPB having another multiple) was prepared. It was diluted with pure water into NPB (n×NPB) different in multiple.

[Preparation of Collagen Sol]

The collagen solution (12 g) in the 15 mL centrifuge tube, prepared as described above, was allowed to stand in a polystyrene foam container filled with crushed ice. A magnetic stirrer (10.8 g, inner diameter: 10 mm×39 mm) for accelerating stirring was housed in the tube. Predetermined amounts of the aqueous genipin solution allowed to stand in a refrigerator of 4° C. and the 10×NPB allowed to stand at room temperature were sucked up with a micropipette, respectively, and added to the centrifuge tube containing the collagen solution. The centrifuge tube was stirred by vigorous shaking. The collagen sol thus obtained was used for ex vivo experiments for submucosal injection using excised porcine stomachs.

[Ex Vivo Experiments for Submucosal Injection using Excised Porcine Stomachs]

From a resected porcine stomach purchased, a specimen having a size of about 50 mm×50 mm was resected. It was attached to a sheet of polystyrene foam with thumbtacks, allowed to stand in an incubator for warming. After confirmation that the surface temperature fell within a range of from 36 to 37° C., the resected stomach was taken out from the incubator, followed by submucosal local injection of the collagen sol through a medical injection needle (23 G).

Figure 3:
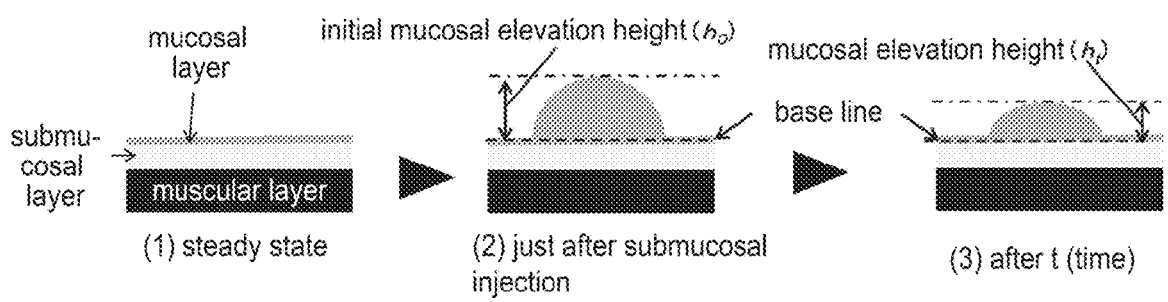
FIG. 3 shows a method of measuring a retention rate of mucosal elevation height in a submucosal local injection test.

As shown in FIG. 3, a retention rate of mucosal elevation height was measured by the following method. An initial elevation height ($h_0$) of the specimen just after the submucosal local injection was measured by taking a photograph of it from a horizontal direction by a digital camera. Then, the resected stomach was promptly returned to the incubator. After a predetermined time (t), the resected stomach was taken out and photographed from a horizontal direction by a digital camera to measure an elevation height ($h_t$). A retention rate of mucosal elevation height was determined based on the following equation:

Retention rate of mucosal elevation height (%)= $h_t/h_0 \times 100$

The resected stomach allowed to stand in the incubator for 60 minutes after the submucosal local injection was, after measurement of the elevation height, immersed in a 4% aqueous paraformaldehyde solution and then placed overnight in a refrigerator of 4° C. It was then immersed in a 10% aqueous sucrose solution and by gradual increase of its concentration to 15% and 20%, sucrose substitution was performed. Then, a frozen block was prepared using a carboxymethyl cellulose embedding agent and a 20-μm thick tissue section was formed with a microtome. After hematoxylin-eosin staining by a conventional method, a tissue image was obtained using an upright microscope ("BX53" product of Olympus).

Example 1

Figure 4:
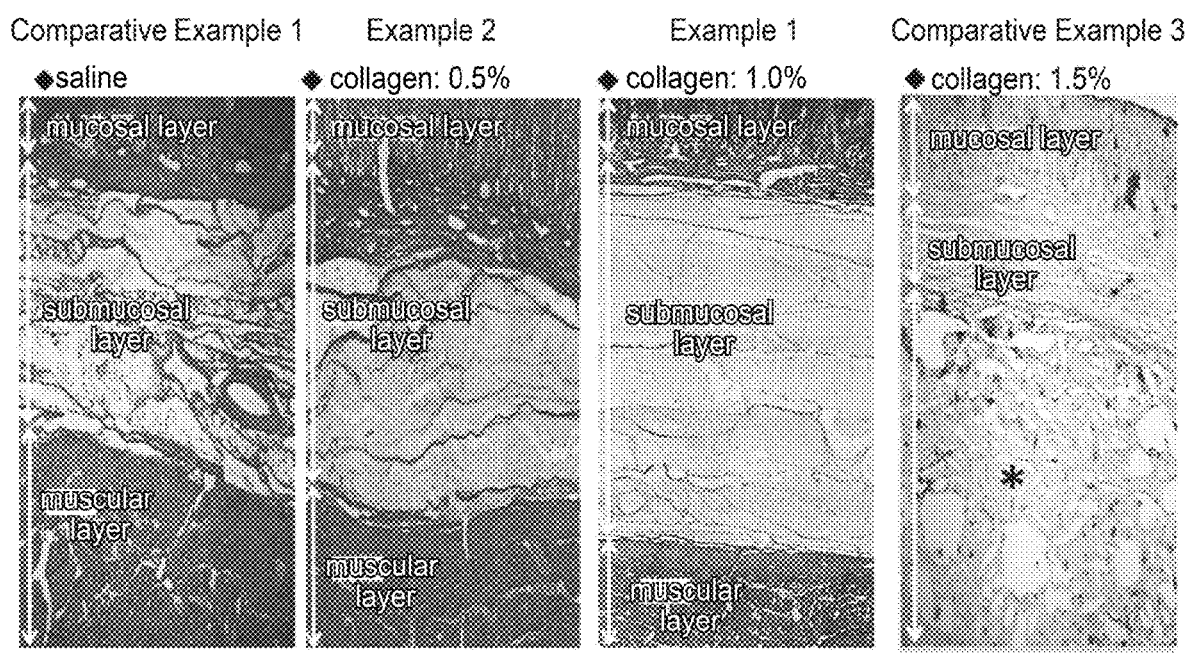
FIG. 4 shows a histological image of a porcine gastric wall 60 minutes after submucosal local injection of various collagen sols or saline.
Figure 5:
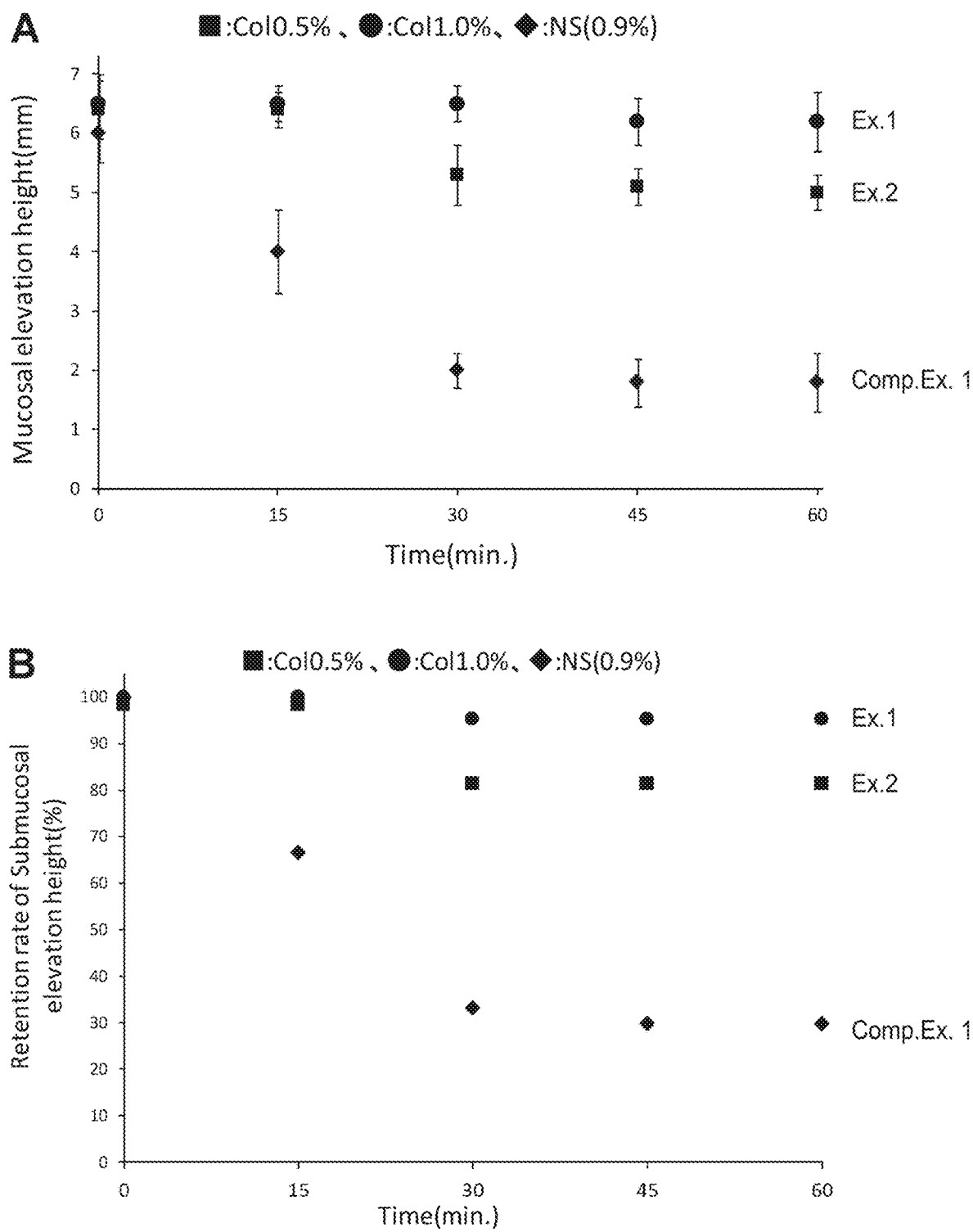
FIG. 5 is a graph showing a time-dependent change of elevation height after injection of genipin-containing collagen sol into the porcine gastric submucosa.

The collagen sol having a composition shown in Table 1 was prepared (genipin concentration: 4 mM (=905 mg/L)). The histological image after submucosal injection of the resulting collagen sol using excised porcine stomachs is shown in FIG. 4, while a time-dependent change of a retention rate of mucosal elevation height is shown in FIG. 5. The locally injected collagen integrated with the submucosal layer created a mucosal elevation. The elevation height after 60 minutes kept 90% or more of the initial height and a statistically significant decrease did not occur during a period from 45 minutes to 60 minutes after the injection.

When bleeding is not so bad, ESD for a single lesion is usually completed within 60 minutes from the local injection of a submucosal local injection to hemostatic treatment so that the retention rate of mucosal elevation height after 60 minutes can be one evaluation standard of a submucosal local injection.

Example 2

In a manner similar to that of Example 1 except that the collagen concentration was reduced from 1.0% to 0.5%, a collagen sol was prepared and ex vivo experiments for submucosal injection using excised porcine stomachs was performed. The histological image after the submucosal local injection is shown in FIG. 4 and a time-dependent change in retention rate of mucosal elevation height is shown in FIG. 5. The locally injected collagen was integrated with the submucosal layer to create a mucosal elevation. The elevation height after 60 minutes kept 80% or more of the initial height.

Example 3

Figure 6:
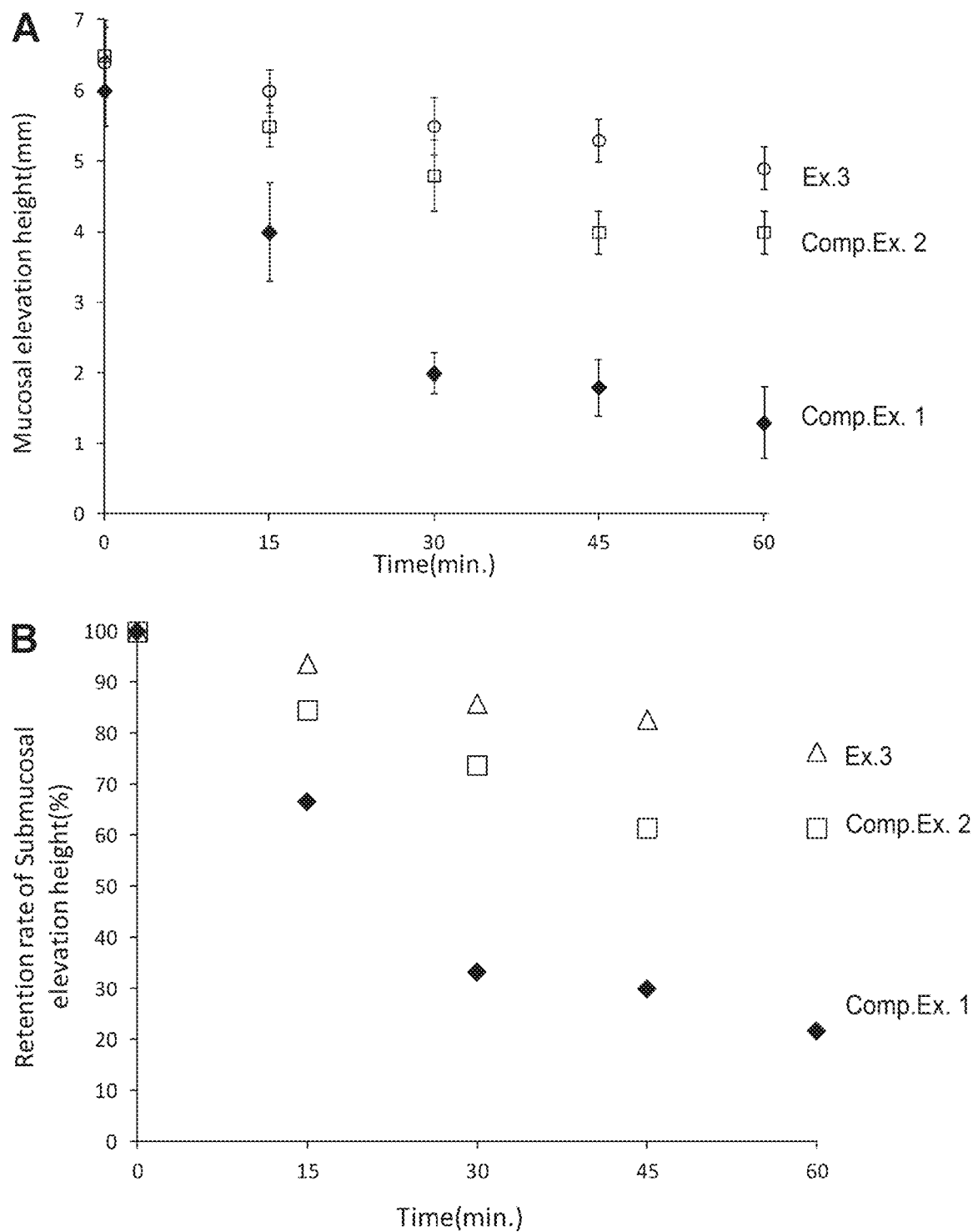
FIG. 6 is a graph showing a time-dependent change of elevation height after local injection of genipin-free collagen sol into the porcine gastric submucosa.

In a manner similar to that of Example 1 except that genipin was not added, a collagen sol was prepared and ex vivo experiments for submucosal injection using excised porcine stomachs was performed. A time-dependent change in retention rate of mucosal elevation height is shown in FIG. 6. As shown in Example 1, at a collagen concentration of 1.0% permitting integration with the submucosal layer, the elevation height after 60 minutes was 70% or more of the initial height and a statistically significant reduction did not occur during a period from 45 minutes to 60 minutes after the injection, even if the sol did not contain genipin.

Comparative Example 1

A histological image after ex vivo experiments for submucosal injection using excised porcine stomachs was performed with saline is shown in FIG. 4 and a time-dependent change in retention rate of mucosal elevation height is shown in FIG. 5. The saline having a low viscosity was integrated with the submucosal layer to create a mucosal elevation. After the submucosal local injection, however, the elevation height decreased promptly and it decreased to less than 70% of the initial height after 15 minutes and even to less than 40% of the initial height after 30 minutes.

Comparative Example 2

In a manner similar to that of Example 3 except the NPB concentration was reduced from 1.6×NPB to 1.0×NPB, a collagen sol was prepared and ex vivo experiments for submucosal injection using excised porcine stomachs was performed. A time-dependent change in retention rate of mucosal elevation height is shown in FIG. 6. Due to a reduction in the concentration of sodium chloride, the fibril formation speed of the collagen decreased and diffusion of the sol was accelerated. As a result, the elevation height after 60 minutes fell below 70% of the initial height.

Comparative Example 3

In a manner similar to that of Example 1 except that the collagen concentration was increased from 1.0% to 1.5%, a collagen sol was prepared and ex vivo experiments for submucosal injection using excised porcine stomachs was performed. A histological image after the submucosal local injection is shown in FIG. 4. Due to an increase in the collagen concentration, the viscosity increased, which prevented integration with the submucosal layer. When such a phenomenon occurs, the submucosal layer hardly expands. As a result, the injection is not effective for facilitating dissection of the submucosal layer and at the same time, it is not suited for the removal of cancer which has infiltrated into the submucosal layer.

TABLE 1

Compositions and evaluation results of collagen sol

| | Composition of collagen sol | | | | | |
|---|---|---|---|---|---|---|
| | pH | Collagen (%) | Genipin (mM) | NPB (n × NPB) | NaCl (mM) | Evaluation |
| Ex. 1 | 7.0 | 1.0 | 4 | 1.6 | 224 | Retention rate of mucosal elevation height: Yes<br>Integration with submucosal layer: Yes |
| Ex. 2 | 7.0 | 0.5 | 4 | 1.6 | 224 | Retention rate of mucosal elevation height: Yes<br>Integration with submucosal layer: Yes |
| Ex. 3 | 7.0 | 1.0 | 0 | 1.6 | 224 | Retention rate of mucosal elevation height: Yes |
| Comp. Ex. 1 | | | saline | | | Retention rate of mucosal elevation height: No |
| Comp. Ex. 2 | 7.0 | 1.0 | 0 | 1.0 | 140 | Retention rate of mucosal elevation height: No |
| Comp. Ex. 3 | 7.0 | 1.5 | 4 | 1.6 | 224 | Integration with submucosal layer: No |

\* Evaluation

Retention rate of mucosal elevation height: Yes: retention rate of mucosal elevation height 60 minutes after submucosal local injection is 70% or more.

Retention rate of mucosal elevation height: No: retention rate of mucosal elevation height 60 minutes after submucosal local injection is less than 70%.

Integration with submucosal layer: Yes: Gel independent from the submucosal layer is not observed from the histological image obtained by tissue fixation 60 minutes after submucosal local injection.

Integration with submucosal layer: No: Gel independent from the submucosal layer is observed from the histological image obtained by tissue fixation 60 minutes after submucosal local injection.

INDUSTRIAL APPLICABILITY

The present invention makes it possible to provide a safe local injection which, when submucosally and locally injected, is promptly integrated with the submucosal layer to cause gelation and creates a mucosal elevation having a high retention rate of mucosal elevation height. The sol of the present invention can be injected/formed into a gel without the necessity of an operation which may cause histological damages or a special apparatus and in addition, different from blood preparations, it is free from contamination or limitation on an amount to be secured. The present invention has industrial applicability in medical fields.

The present application claims priority to Japanese Patent Application No. 2016-224258 filed on Nov. 17, 2016 and the entire content thereof is hereby incorporated by reference.

What is claimed is:

1. A method of treating a submucosa, which comprises injecting a sol comprising from 0.2 mass % to 1.2 mass % of a collagen, water, a buffer, and from 220 mM to 310 mM sodium chloride into the submucosa, wherein denaturation temperature of the collagen is 37° C. or more and 50° C. or less.

2. The method according to claim 1, wherein the sol further comprises from 40 mg/L to 1400 mg/L of genipin or a genipin derivative.

3. The method according to claim 1, wherein the sol has a pH from 6.0 to 9.0 and the buffer contains a phosphate.

4. The method according to claim 1, wherein the sol comprises from 40 mg/L to 1400 mg/L of genipin or a genipin derivative.

5. An endoscope system for endoscopic mucosal resection or endoscopic submucosal dissection, comprising a unit for locally injecting a sol comprising from 0.2 mass % to 1.2 mass % of a collagen, water, a buffer, and from 220 mM to 310 mM sodium chloride, wherein denaturation temperature of the collagen is 37° C. or more and 50° C. or less.

6. The method according to claim 3, wherein the sol comprises from 40 mg/L to 1400 mg/L of genipin or a genipin derivative.

7. The method according to claim 1, wherein the sol forms a gel when injected.

8. The method according to claim 1, wherein the sol results in a mucosal elevation when locally injected into the submucosa.

9. The system according to claim 5, wherein the sol further comprises from 40 mg/L to 1400 mg/L of genipin or a genipin derivative.

10. The system according to claim 5, wherein the sol has a pH from 6.0 to 9.0 and the buffer contains a phosphate.

11. The system according to claim 5, wherein the sol forms a gel when injected.

12. The system according to claim 5, wherein the sol results in a mucosal elevation when locally injected into the submucosa.

\* \* \* \* \*